United States Patent
Galbreath et al.

(10) Patent No.: US 9,103,747 B2
(45) Date of Patent: Aug. 11, 2015

(54) VEHICULAR DYNAMIC RIDE SIMULATION SYSTEM USING A HUMAN BIOFIDELIC MANIKIN AND A SEAT PRESSURE DISTRIBUTION SENSOR ARRAY

(75) Inventors: Ashford Allen Galbreath, Troy, MI (US); Terry O'Bannon, Royal Oak, MI (US)

(73) Assignee: Lear Corporation, Southfield, MI (US)

( * ) Notice: Subject to any disclaimer, the term of this patent is extended or adjusted under 35 U.S.C. 154(b) by 144 days.

(21) Appl. No.: 12/908,504

(22) Filed: Oct. 20, 2010

(65) Prior Publication Data

US 2012/0096960 A1 Apr. 26, 2012

(51) Int. Cl.
| | |
|---|---|
| *G01M 7/08* | (2006.01) |
| *G01M 99/00* | (2011.01) |
| *G01M 7/02* | (2006.01) |
| *A61B 5/103* | (2006.01) |
| *A61B 5/00* | (2006.01) |
| *B60N 2/00* | (2006.01) |
| *B60N 2/60* | (2006.01) |

(52) U.S. Cl.
CPC ........... *G01M 99/001* (2013.01); *A61B 5/1036* (2013.01); *A61B 5/6891* (2013.01); *A61B 5/6893* (2013.01); *B60N 2/002* (2013.01); *B60N 2/60* (2013.01); *G01M 7/025* (2013.01); *G01M 7/08* (2013.01); *A61B 2562/0247* (2013.01); *A61B 2562/046* (2013.01)

(58) Field of Classification Search
CPC ...... G01M 7/025; G01M 7/08; G01M 99/001
USPC .......................................... 73/862.046, 865.1
See application file for complete search history.

(56) References Cited

U.S. PATENT DOCUMENTS

| | | | |
|---|---|---|---|
| 3,010,223 | A | 11/1961 | Alderson |
| 3,818,756 | A * | 6/1974 | Barron et al. .................... 73/172 |
| 3,890,723 | A | 6/1975 | Haurat et al. |
| 3,985,960 | A | 10/1976 | Wallace, Jr. |
| 3,999,309 | A | 12/1976 | Ganzalez |
| 4,060,696 | A | 11/1977 | Iwahara et al. |
| 4,068,091 | A | 1/1978 | Doi |
| 4,388,494 | A | 6/1983 | Schone et al. |

(Continued)

FOREIGN PATENT DOCUMENTS

| | | |
|---|---|---|
| CN | 101251959 A | 8/2008 |
| CN | 101739857 A | 6/2010 |

(Continued)

OTHER PUBLICATIONS

"A Brief Guide to Microphones," 2000, Audio-Tchnica, available on the Internet at http://www.audiotechnica.com/using/mphones/guide/micdoes.html.

(Continued)

*Primary Examiner* — Paul West
(74) *Attorney, Agent, or Firm* — MacMillan, Sobanski & Todd, LLC

(57) ABSTRACT

A system that generates a dynamic seating body pressure distribution data includes a seat and a stimulus applying mechanism that is adapted to apply a stimulus to the seat. A human biofidelic manikin is provided on the seat. A seat pressure distribution sensor array is responsive to the human biofidelic manikin for generating a dynamic seating body pressure distribution data when the stimulus applying mechanism applies a stimulus to the seat.

14 Claims, 5 Drawing Sheets

(56) References Cited

U.S. PATENT DOCUMENTS

| | | |
|---|---|---|
| 4,441,576 A | 4/1984 | Allen |
| 4,451,416 A | 5/1984 | Burtscher |
| 4,586,194 A | 4/1986 | Kohashi et al. |
| 4,631,962 A | 12/1986 | Genuit |
| 4,680,856 A | 7/1987 | Zuccarelli |
| 4,701,132 A | 10/1987 | Groesch et al. |
| 4,739,513 A | 4/1988 | Kunugi |
| 4,773,865 A | 9/1988 | Baldwin |
| 4,944,681 A | 7/1990 | Burgio et al. |
| 5,031,216 A | 7/1991 | Gorike et al. |
| 5,320,571 A | 6/1994 | Lo |
| 5,465,469 A | 11/1995 | Sakai et al. |
| 5,526,707 A | 6/1996 | Smrcka |
| 5,583,942 A | 12/1996 | Van Der Berg |
| 5,628,230 A | 5/1997 | Flam |
| 5,661,812 A | 8/1997 | Scofield et al. |
| 5,741,989 A | 4/1998 | Viano et al. |
| 5,753,834 A * | 5/1998 | Stewart ........................ 73/865.3 |
| 5,928,160 A | 7/1999 | Clark et al. |
| 6,009,750 A | 1/2000 | Maurer et al. |
| 6,101,432 A | 8/2000 | Her et al. |
| 6,116,102 A | 9/2000 | Faust et al. |
| 6,131,436 A | 10/2000 | O'Bannon et al. |
| 6,139,507 A | 10/2000 | Jeng |
| 6,206,703 B1 | 3/2001 | O'Bannon |
| 6,220,089 B1 | 4/2001 | Gu et al. |
| 6,360,607 B1 | 3/2002 | Charette et al. |
| 6,386,054 B1 * | 5/2002 | Jones et al. ................. 73/865.3 |
| 6,392,550 B1 | 5/2002 | Najor |
| 2002/0005638 A1 | 1/2002 | Musiol et al. |
| 2002/0083783 A1 | 7/2002 | Ahn |
| 2004/0011150 A1 | 1/2004 | Reynolds et al. |
| 2005/0277092 A1 | 12/2005 | Hwang |

FOREIGN PATENT DOCUMENTS

| | | |
|---|---|---|
| DE | 3102965 C2 | 3/1983 |
| EP | 57287 A1 | 8/1982 |
| EP | 126783 A1 | 12/1984 |
| GB | 2231433 A | 11/1990 |
| JP | 03168000 A | 7/1991 |
| JP | 2000276040 A | 10/2000 |
| WO | 9830995 A1 | 7/1998 |

OTHER PUBLICATIONS

"A New Dummy for Vibration Transmissibility Measurement in Improving Ride Comfort," 1999, Yi Gu, Lear Corporation, International Congress and Exposition, Detroit, Michigan, Mar. 1-4, 1999.

Arendt et al., "Review of Anthropomorphic Test Device Instrumentation, Data Processing, and Certification Test Procedures," Dec. 1984, pp. 1-64.

"Creating a Biofidelic Seating Surrogate," 1999-01-0627, Dan Adams, International Congress and Expositions, Detroit, Michigan, Mar. 1-4, 1999.

Elsea, Peter, "Microphones," 1996, available on the Internet at http://arts.ucsc.edu/EMS/Music/tech_background/TE-20/teces_20.html.

"HMS III.L Head Measurement System," Head Acoustics, GmbH, Mar. 1999, pp. 1-2.

"HMS III.O Head Measurement System," Head Acoustics, GmbH, May 2001, pp. 1-4.

Jay et al., "The Development of a Biofidelic Mannequin with Binaural Sensing Capability," May 2001, Florence ATA 2001—7th International Conference—The Role of Experimentation in the Automotive Product Development Process, pp. 1-12.

"KU-100 Operating Instructions," May 2002, Georg Neumann GmbH, pp. 1-20.

"KU-100 Dummy Head Product Information," Nov. 2000, Georg Neumann GmbH, pp. 1-4.

Le Claire et al., "The Safety of Wheelchair Occupants in Toad Passenger Vehicles," 2003, pp. 1-144.

Maltese, M., "2002 SAE Govt/Industry Meeting," 2002, pp. 1-4. available on the Internet at http://www.nrd.nhtsa.dot.org.

"Measurements of Comfort in Vehicles," Silva, M.C. Gameiro, Measurement Science and Technology, 2002, pp. R41-R60.

O'Bannon et al., "Creating a Biofidelic Seating Surrogate," Mar. 1999, SAE International, pp. 1-4.

Peud, S., "Natural Listening With a Dummy Head," Jul. 1985, Georg Neumann GmbH, pp. 1-6.

Chinese First Office Action, Application No. 201110320587.0 dated Nov. 21, 2014.

M. Jay et al., Excitation and Measurement of BSR in Vehicle Seats, Lear Technologies L.L.C., Sound Quality and Vibration & Harshness Groups, 01NVC-25, Society of Automotive Engineers, Inc., Copyright 2001 (admitted prior art).

* cited by examiner

VEHICULAR DYNAMIC RIDE SIMULATION SYSTEM USING A HUMAN BIOFIDELIC MANIKIN AND A SEAT PRESSURE DISTRIBUTION SENSOR ARRAY

BACKGROUND OF THE INVENTION

This invention relates in general to a test fixture for accurately simulating a seating environment within a vehicle and for measuring seat pressure data in response to simulated operation of the vehicle. In particular, this invention relates to a vehicular dynamic ride simulation system that includes both a human biofidelic manikin and a seat pressure distribution sensor array for collecting and displaying dynamic pressure distribution data over a period of time and a variety of operating conditions.

Virtually all vehicles include at least one seat upon which an occupant of the vehicle sits during operation of the vehicle. Such a seat is a primary interface between the occupant and the vehicle. Therefore, it is very important that the seat function not only in a safe and reliable manner, but that it also provide maximum amount of comfort to the occupant thereon. Because of this, seat manufacturers devote a significant amount of their resources to design seats that are comfortable for use within vehicles.

To facilitate the design process, it is important to gather accurate data regarding the operation of a seat during operation of the vehicle. In one known data-gathering method, a human test subject sits upon a seat that is provided within an actual vehicle as it is operated on a road. In a similar known data-gathering method, the human test subject sits upon a seat that is provided within a test fixture which is subjected to a variety of mechanical stimuli that simulate the operation of the vehicle on a road. In both of these known data-gathering methods, a single pressure sensor has been provided that measures the total amount of pressure that is exerted on the entire seat in response to the operation of the vehicle (whether actually on the road or simulated). Although these total pressure sensing systems can provide some useful information to a seat designer, they lack the ability to provide sufficiently detailed information as to how individual areas of the seat will function under highly dynamic conditions.

It is also known to measure a static seating pressure distribution characteristic of a human test subject on a seat. Such a static seating pressure distribution characteristic is essentially a two dimensional representation of the amount of pressure that is exerted by the human test subject upon each of a plurality of individual areas defined on the seat at a single point in time. The measurement of this static seating body pressure distribution characteristic has been accomplished using a relatively flat mat that contains a plurality of individual pressure sensors arranged in a two-dimensional array. Each of the individual pressure sensors within the mat represents an individual area of interest on the seat. Initially, the mat is placed upon a surface of the seat for which measurements are desired to be taken. Then, the human test subject sits upon the mat in a motionless manner. The individual pressure sensors of the mat generate a plurality of individual pressure signals that are used to create the static seating body pressure distribution characteristic. Although this static seating body pressure distribution can provide a quick and economical check to determine if excessive static pressure points exist relative to anatomical landmarks, it has been found that a seat can have comfortable pressure levels under static conditions but still undesirably allow some portions of the occupant to hit a "hard" surface (such as an underlying frame of the seat) under highly dynamic conditions, such as when the vehicle is operated on a relatively rough road.

The adoption of new, thinner-foam technologies in vehicle seats has been hampered by a concern that portions of an occupant of the seat may undesirably "bottom out" on the underlying frame when the vehicle is operated over a relatively rough road. Conventional data-gathering methods, such as those described above, have not proven to be adequate for providing the dynamic seating body pressure distribution data that is needed to resolve this concern. Thus, it would be desirable to provide a vehicular dynamic ride simulation system that includes both a human biofidelic manikin and a seat pressure distribution sensor array for collecting pressure distribution data over a period of time and a variety of operating conditions.

SUMMARY OF THE INVENTION

This invention relates to a system for simulating a dynamic ride environment within a vehicle that includes both a human biofidelic manikin, which can exert a human-like pressure distribution upon a seat and react in a human-like manner to dynamic operating stimuli generated by the test fixture, and a seat pressure distribution sensor array, which can sense and measure the dynamic seating pressure distribution characteristic of that human biofidelic manikin across the seat during those dynamic operating stimuli and a variety of operating conditions.

Various aspects of this invention will become apparent to those skilled in the art from the following detailed description of the preferred embodiment, when read in light of the accompanying drawings.

DETAILED DESCRIPTION OF THE PREFERRED EMBODIMENT

Figure 1:
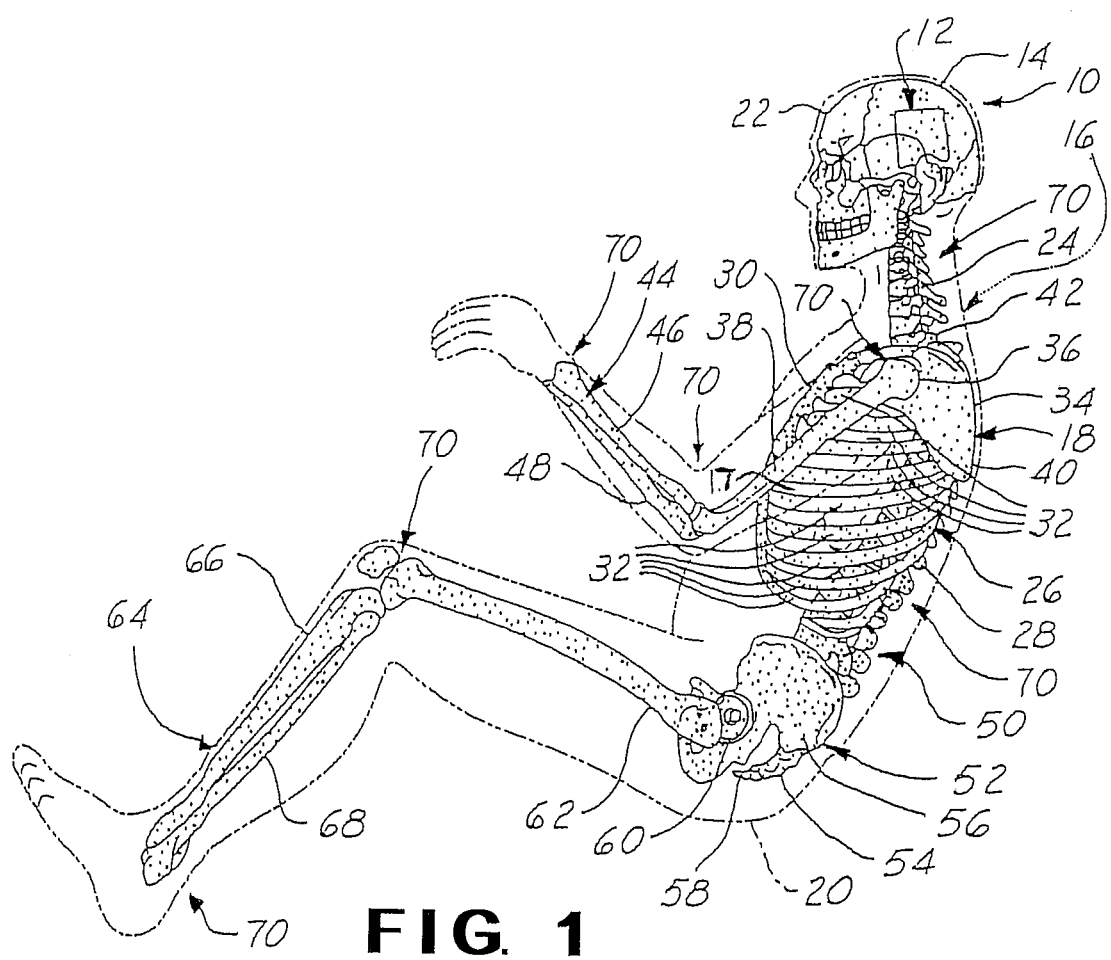
FIG. 1 is a side elevational view of a human biofidelic manikin that constitutes a first portion of a system for simulating a dynamic ride environment within a vehicle in accordance with this invention.

Referring now to the drawings, there is illustrated in FIG. 1 a human biofidelic manikin, indicated generally at 10, that constitutes a first portion of a system for simulating a dynamic ride environment within a vehicle in accordance with this invention. The human biofidelic acoustical manikin 10 may, if desired, be the same as described and illustrated in U.S. Published Patent Application No. 2004/0101815 (owned by the assignee of this invention), and the disclosure of that published patent application is incorporated herein by reference. However, as will become apparent below, the human biofidelic manikin 10 of this invention need not include any of the specific structures described in detail in that published patent application. Rather, all that is required of the human biofidelic manikin 10 of this invention is that the relevant portions thereof (i.e., the portions that engage or otherwise cooperate with the other portions of the system for simulating a dynamic ride environment within a vehicle) accurately represent a human being. Typically, those relevant portions of the human biofidelic manikin 10 will accurately represent a human being in size, shape, weight, and response to mechanical stimuli.

The illustrated human biofidelic manikin 10 may, as described in detail in the above-referenced published patent application, include a binaural sensing system, indicated generally at 12, for in-situ binaural testing. However, the binaural sensing system 12 may be omitted if desired. The illustrated human biofidelic manikin 10 include a biofidelic head 14, although again such is not required for the purposes of this invention. A biofidelic body, indicated generally at 16, is coupled to the head 14. The body 16 has a skeletal frame structure, indicated generally at 18, having a density, mass, geometry, and compliance that substantially corresponds with that of a human. A biofidelic skin 20 covers the body 16. The skin 20 has substantially anatomically correct surface geometry, density, and compliance as that of a human. The head 14, the body 16, and the skin 20 may be formed of plastic, metal, or other desired material.

The skeletal structure 18 includes a skull 22, a set of cervical vertebrae 24 that is connected to the skull 22, and a thoracic cage 26 that is coupled to the cervical vertebrae 24. The thoracic cage 26 includes a set of thoracic vertebrae 28, a sternum 30, and a set of ribs 32 that interconnect the thoracic vertebrae 28 and the sternum 30. The skeletal structure 18 also includes a pectoral girdle 34 and a pair of ball-and-socket joints 36 (only one is illustrated) for connecting respective humeri 38 (only one is illustrated) on opposite sides of the thoracic cage 26. The pectoral girdle 34 includes a pair of scapulae 40 (only one is illustrated) that are connected at opposite sides of the thoracic cage 26 and a pair of clavicles 42 (only one is illustrated) that are connected to their respective scapulae 40. A pair of forearms, indicated generally at 44 (only one is illustrated) are coupled to their respective humeri 38. Each of the forearms 44 includes a radius 46 and an ulna 48 that are hingely connected to its respective humerus 38.

A set of lumbar vertebrae, indicated generally at 50, interconnect the thoracic cage 26 to a pelvic girdle, indicated generally at 52. The pelvic girdle 52 includes a set of sacrum vertebrae 54 and a pair of ilium 56 (only one is illustrated). A coccyx 58 is connected to the sacrum vertebrae 54. A pair of ball-and-socket joints 60 (only one is illustrated) connect respective femurs 62 (only one shown) to their respective ilium 56. The femurs 62 constitute upper portions of respective legs, indicated generally at 64 (only one is illustrated in FIG. 1). Each of the legs 64 also includes a tibia 66 (only one is illustrated) and a fibula 68 (only one is illustrated). Each of the tibiae 66 is hingely connected to its respective femur 62.

As in a human body, the illustrated human biofidelic manikin 10 includes a plurality of joints 70, some of which are described above. The joints 70 of the human biofidelic manikin 10 have substantially correct response characteristics as a human body, including proper mass and stiffness. The illustrated joints 70, in conjunction with the other structural body members discussed above, provide proper stiffness distributions throughout the human biofidelic manikin 10. The joints 70 may be of various style, shape, type, and size. Such joints 70 may include elbow joints, knee joints, wrist joints, knuckle joints, ankle joints, and other joints. The joints 70 may also be part of a series or set of joints, such as vertebrae within a neck or a spine. Any location within the human biofidelic manikin 10 where one part can be moved in relation to an adjacent part may be considered a joint. The mass and stiffness of the joints 70 may be varied by adjusting density, mass, type of material, chemical make-up, size, shape, or other joint parameter known in the art.

The skin 20 of the human biofidelic manikin 10, which may be in the form of elastomeric plastic, preferably has the same mechanical properties as bulk muscular tissue in a state of moderate contraction. The mechanical properties include stiffness, inertia, and damping. For example, the skin 20 may have an effective stiffness within a range of approximately 6 kPa to 140 kPa. This stiffness range is not critical for generating a substantially correct response for collection of dynamic vibrational data. Therefore, the stiffness may vary outside this range as long as mass is also adjusted to compensate for the variance. In doing so, a substantially correct response may be achieved, but static and impact performance of the human biofidelic manikin 10 may be degraded.

Figure 2:
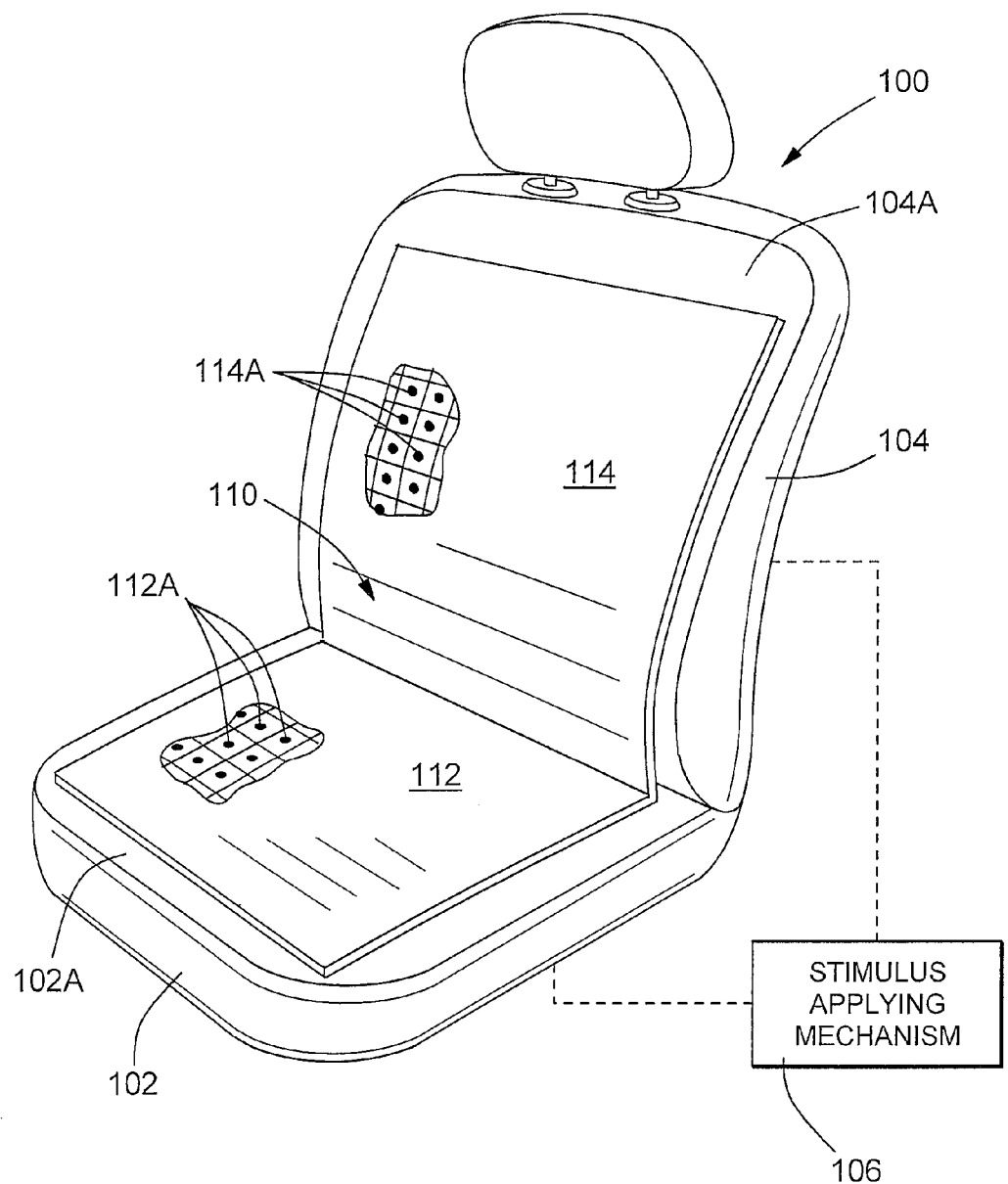
FIG. 2 is a perspective view of a seat having a pressure distribution sensor array provided thereon that constitutes a second portion of the system for simulating a dynamic ride environment within a vehicle in accordance with this invention.

FIG. 2 is a perspective view of a seat, indicated generally at 100, that includes a seat bottom 102 having an exterior surface 102a and a seat back 104 having an exterior surface 104a. Although this invention will be described and illustrated in connection with both the seat bottom 102 and the seat back 104, it will be appreciated that this invention may be practiced in connection with only the seat bottom 102, only the seat back 104, or both the seat bottom 102 and the seat back 104 as desired. The illustrated seat back 104 is connected in a conventional manner to the seat bottom 102 for pivoting movement relative thereto, although such is not required. The illustrated seat 100 is intended to represent any type of seat upon which an occupant of a vehicle may be seated. Therefore, this invention is not limited to the specific shape and structure of the illustrated seat 100.

It is preferred that the seat 100 be provided as part of a test fixture that can include, among other things, a stimulus applying mechanism 106 for applying one or more stimuli to either or both of the seat bottom 102 and the seat back 104. The stimulus applying mechanism 106 can be embodied as any desired structure that can apply a stimulus, such as a mechanical impulse, vibration, or other movement, to either or both of the seat bottom 102 and the seat back 104. For example, the stimulus applying mechanism 106 can be embodied as a conventional six-axis shaker table having mechanical, hydraulic, or pneumatic actuators that can apply the desired stimulus to the seat 100. Alternatively, the seat 100 can be provided as part of an actual vehicle that can be operated on a road.

FIG. 2 also illustrates a pressure distribution sensor array, indicated generally at 110, provided on the seat 100 that constitutes a second portion of the system for simulating a dynamic ride environment within a vehicle in accordance with this invention. The illustrated pressure distribution sensor array 110 includes a seat bottom pressure distribution sensor array 112 that is associated with the seat bottom 102. As will be explained in greater detail below, the seat bottom pressure distribution sensor array 112 is provided to sense a distribution of pressure across some or all of the seat bottom 102 during the operation of the system for simulating a dynamic ride environment within a vehicle of this invention. In the illustrated embodiment, the seat bottom pressure distribution sensor array 112 is supported on the exterior surface 102a of the seat bottom 102. However, it will be appreciated that the seat bottom pressure distribution sensor array 112 may be provided at any desired location on the exterior of the seat bottom 102. Additionally, the seat bottom pressure distribution sensor array 112 may be provided within the interior of the seat bottom 102 if desired.

In the illustrated embodiment, the seat bottom pressure distribution sensor array 112 is embodied as a relatively flat mat that is relatively flexible. As shown in FIG. 2, a plurality of individual pressure sensors 112a are spaced throughout the seat bottom pressure distribution sensor array 112. The number and relative locations of the individual pressure sensors 112a may be determined as desired. The individual pressure sensors 112a respectively define a plurality of individual areas of interest within the seat bottom pressure distribution sensor array 112. The individual pressure sensors 112a of the seat bottom pressure distribution sensor array 112 are, of themselves, conventional in the art and generate a respective plurality of individual pressure signals that are representative of the amount of pressure applied thereto, as will be described in greater detail below. However, the seat bottom pressure distribution sensor array 112 may be embodied as any desired structure that is capable of sensing the pressure distribution across some or all of the seat bottom 102 during the operation of the system for simulating a dynamic ride environment within a vehicle of this invention.

Similarly, the illustrated pressure distribution sensor array 110 also includes a seat back pressure distribution sensor array 114 that is associated with the seat back 104. As will be explained in greater detail below, the seat back pressure distribution sensor array 114 is provided to sense a distribution of pressure across some or all of the seat back 104 during the operation of the system for simulating a dynamic ride environment within a vehicle of this invention. In the illustrated embodiment, the seat back pressure distribution sensor array 114 is supported on the exterior surface 104a of the seat back 104. However, it will be appreciated that the seat back pressure distribution sensor array 114 may be provided at any desired location on the exterior of the seat back 104. Additionally, the seat back pressure distribution sensor array 114 may be provided within the interior of the seat back 104 if desired.

In the illustrated embodiment, the seat back pressure distribution sensor array 114 is embodied as a relatively flat mat that is relatively flexible. As shown in FIG. 2, a plurality of individual pressure sensors 114a are spaced throughout the seat back pressure distribution sensor array 114. The number and relative locations of the individual pressure sensors 114a may be determined as desired. The individual pressure sensors 114a respectively define a plurality of individual areas of interest within the seat back pressure distribution sensor array 114. The individual pressure sensors 114a of the seat back pressure distribution sensor array 114 are, of themselves, conventional in the art and generate a respective plurality of individual pressure signals that are representative of the amount of pressure applied thereto, as will be described in greater detail below. However, the seat back pressure distribution sensor array 114 may be embodied as any desired structure that is capable of sensing the pressure distribution across some or all of the seat back 104 during the operation of the system for simulating a dynamic ride environment within a vehicle of this invention. One example of a device that can function as the seat bottom pressure distribution sensor array 112 and/or the seat back pressure distribution sensor array 114 is the seating/positioning pressure mapping system that is commercially available from Tekscan, Inc. of South Boston, Mass. under the trade name CONFORMat®.

Figure 3:
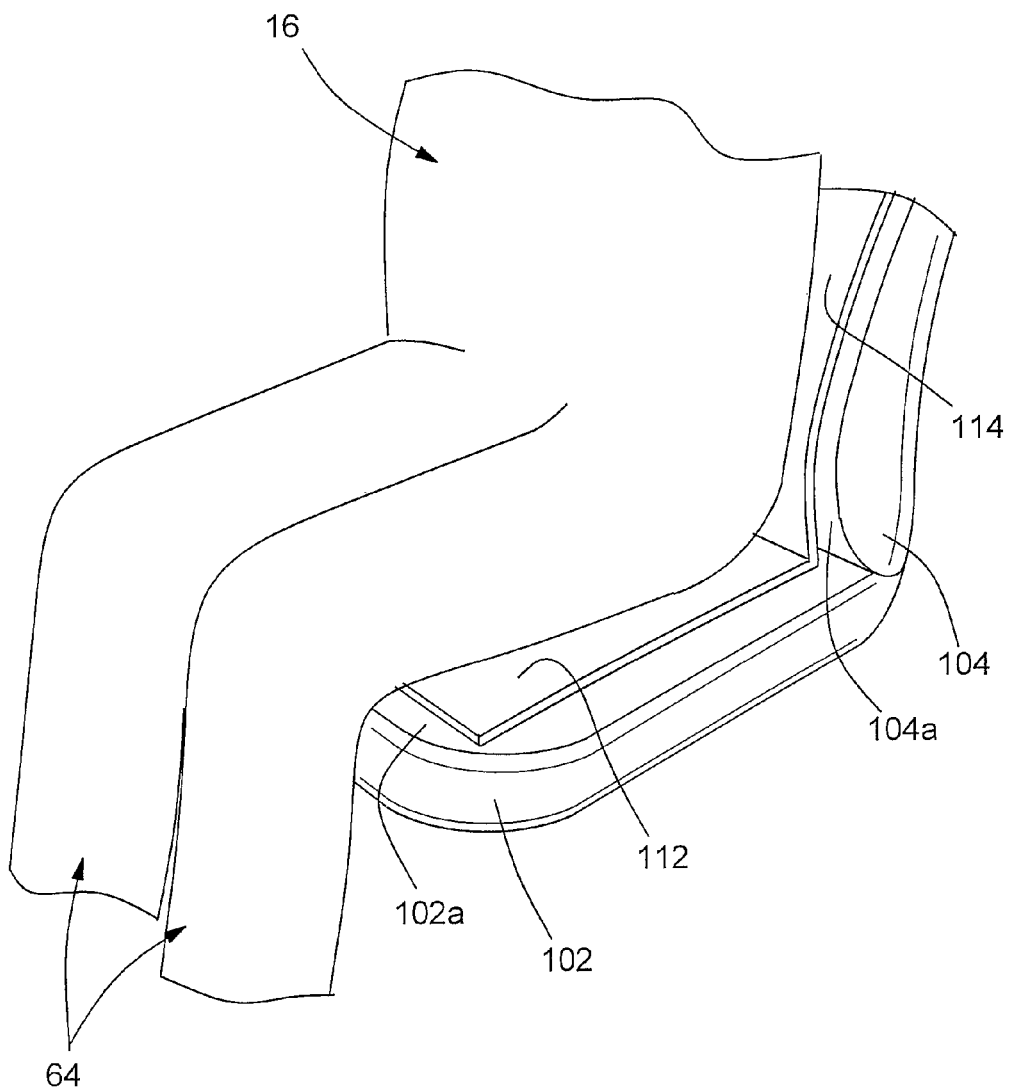
FIG. 3 is an enlarged perspective view of a portion of the human biofidelic manikin illustrated in FIG. 1 disposed upon a portion of the seat pressure distribution sensor array illustrated in FIG. 2.

FIG. 3 shows a portion of the human biofidelic manikin 10 illustrated in FIG. 1 disposed upon a portion of the pressure distribution sensor array 110 illustrated in FIG. 2 to provide the system for simulating a dynamic ride environment within a vehicle in accordance with this invention. The weight of the human biofidelic manikin 10 inherently exerts a pressure distribution across the seat bottom 102 or the seat back 104 (or both) when positioned thereon. That static seating pressure distribution characteristic can be measured by the seat bottom pressure distribution sensor array 112 and/or the seat back pressure distribution sensor array 114. However, as discussed above, such a static seating pressure distribution characteristic cannot provide sufficiently detailed information as to how individual areas of the seat will function under highly dynamic conditions.

Figure 4:
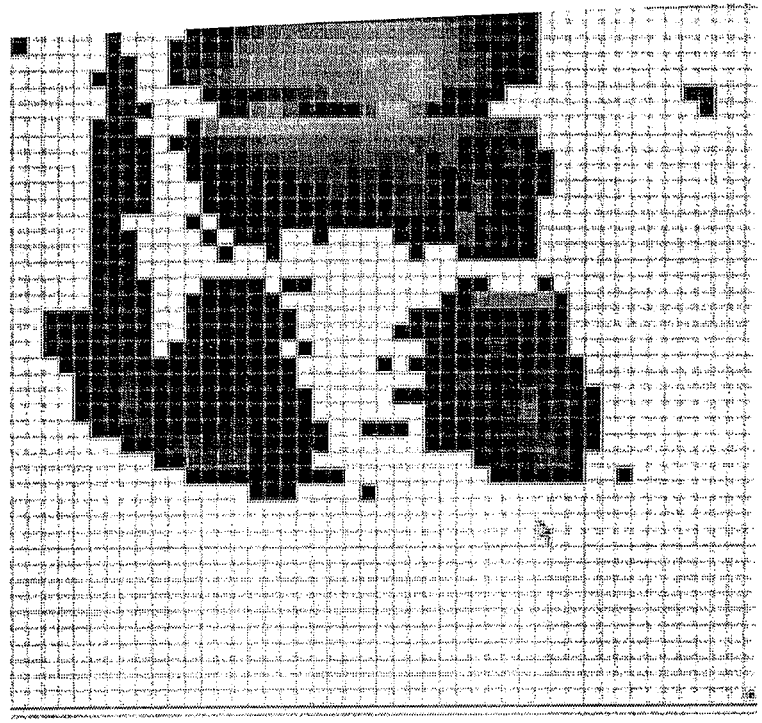
FIG. 4 is a schematic illustration of a first example of a pressure distribution measurement that can be made by the system for simulating a dynamic ride environment within a vehicle in accordance with this invention.

FIG. 4 is a schematic illustration of a first pressure distribution measurement made by the system when the stimulus applying mechanism 106 is not operated or is operated to apply a mechanical stimulus of a relatively small magnitude. As shown therein, the first pressure distribution measurement illustrated in FIG. 4 represents a pressure distribution measurement of a relatively small amount of force that is exerted by the human biofidelic manikin 10 across the seat bottom 102 (or, alternatively, the seat back 104) in response to the mechanical stimulus of a relatively small magnitude. As shown therein, the magnitudes of the pressures sensed by each of the individual pressure sensors 112a and 114a are relatively small.

Figure 5:
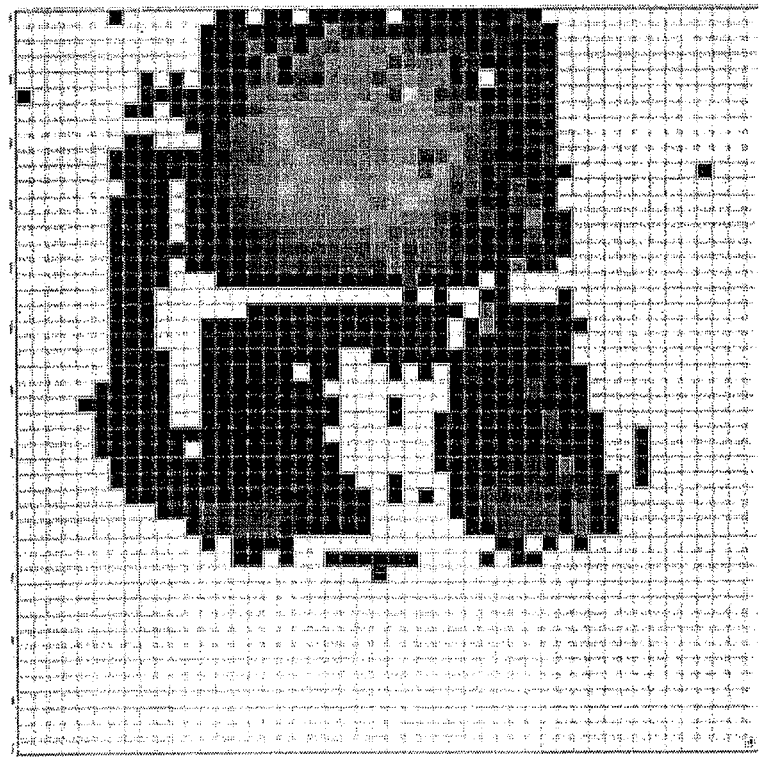
FIG. 5 is a schematic illustration of a second example of a pressure distribution measurement that can be made by the system for simulating a dynamic ride environment within a vehicle in accordance with this invention.

FIG. 5, on the other hand, is a schematic illustration of a second pressure distribution measurement made by the system when the stimulus applying mechanism 106 is operated or is operated to apply a mechanical stimulus of a relatively large magnitude. As shown therein, the second pressure distribution measurement illustrated in FIG. 5 represents a pressure distribution measurement of a relatively large amount of force that is exerted by the human biofidelic manikin 10 across the seat bottom 102 (or, alternatively, the seat back 104) in response to the mechanical stimulus of a relatively large magnitude. As shown therein, the magnitudes of the pressures sensed by each of the individual pressure sensors 112a and 114a are relatively large.

As shown in FIGS. 4 and 5, each of the first and second pressure distribution measurements can be illustrated as a two dimensional array of individual pressure measurement regions. Each of the individual pressure measurement regions within the two dimensional array represents a corresponding area on the associated one of the individual pressure sensors 112a and 114a respectively provided within the pressure distribution sensor arrays 112 and 114. Thus, each of the individual pressure measurement regions represents the magnitude of the pressure that is exerted by the human biofidelic manikin 10 at any given point in time. The magnitudes of these actual pressure measurements can be expressed in any desired manner. For example, the magnitudes of these actual pressure measurements can be shown in different shades of gray (as shown in the illustrated embodiment), different colors, or any other distinguishable manner.

The system of this invention measures the changes in the pressure distribution across the seat bottom 102 and/or the seat back 104 at different points in time and in response to different mechanical stimuli applied by the stimulus applying mechanism 106 and generates pressure distribution measurements in accordance with such measurements. Thus, the system of this invention provides a dynamic seating body pressure distribution data that has been found to be very useful in the design of seats for vehicles, as described above. By applying a variety of mechanical stimuli to the seat 100 over a period of time, a variety of dynamic pressure measurements can be made by the pressure distribution sensor array 110 to provide the desired dynamic seating body pressure distribution data. It should be noted that the pressure distribution measurements that are illustrated in FIGS. 4 and 5 are purely exemplary in nature and, therefore, are not intended to limit the scope of this invention in any manner.

It is known that all mechanical bodies have a natural resonant frequency at which they tend to vibrate when subjected to cyclical mechanical stimuli. This natural resonant frequency is an inherent characteristic of the mechanical body and is based upon many factors, including its composition, size, and shape. In the context of this invention, the combined system of the human biofidelic manikin 10 and the seat 100 upon which the human biofidelic manikin 10 is disposed has such a natural resonant frequency. More significantly, each of the individual areas of interest on the seat 100 (which are defined by the individual pressure sensors 112*a* and 114*a*) will have a unique natural resonant frequency that is based upon (among other things) the specific amount of weight and geometry of the localized portion of the human biofidelic manikin 10 that is disposed thereon.

Figure 6:
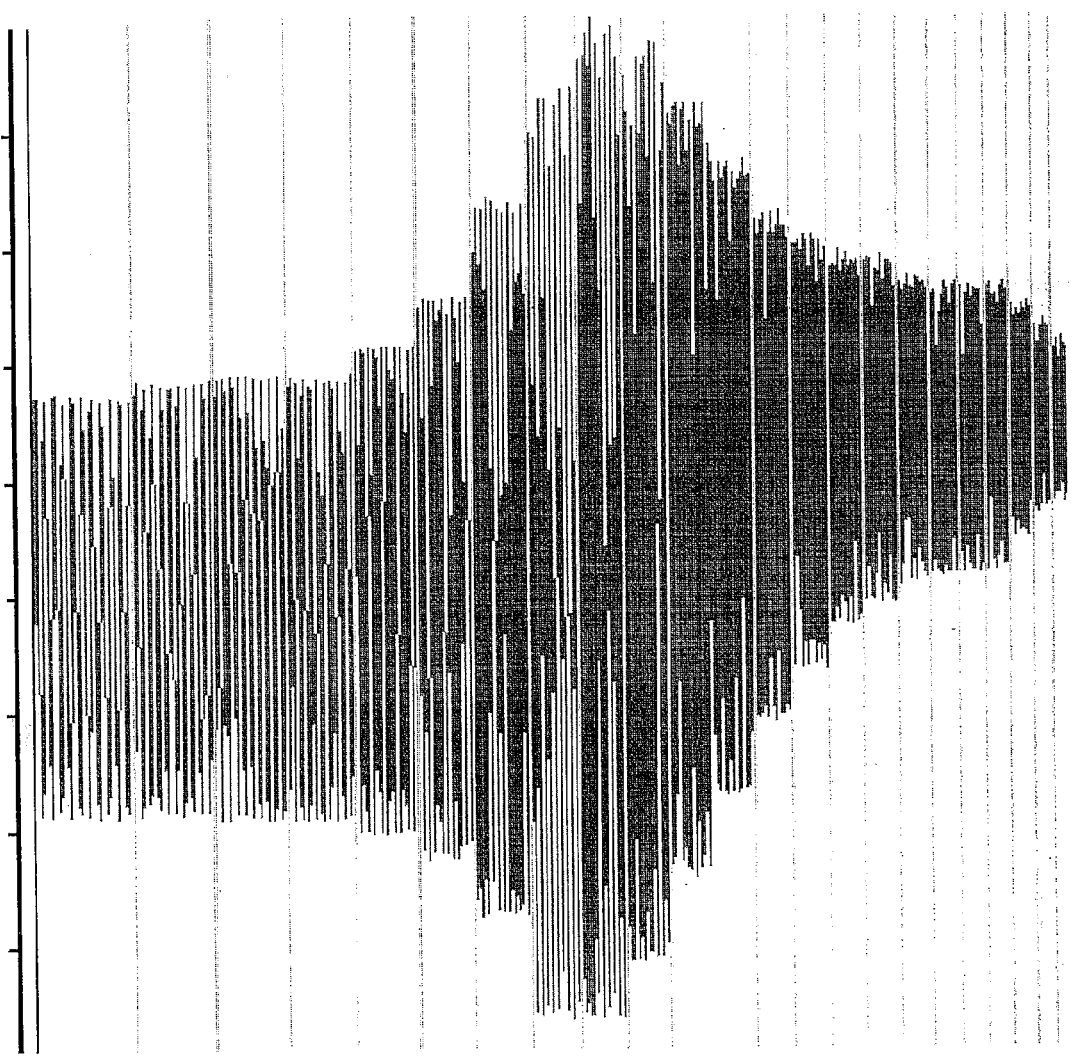
FIG. 6 is a graph that illustrates an exemplary relationship between the amount of pressure that is sensed by a single one of the individual pressure sensors of the seat pressure distribution sensor array illustrated in FIG. 2.

FIG. 6 is a graph that illustrates an exemplary relationship between the amount of pressure that is sensed by a single one of the individual pressure sensors 112*a* and 114*a* of the seat pressure distribution sensor array illustrated in FIG. 2 as a function of frequency of the mechanical stimuli applied thereto. The graph is intended to illustrate that in this single individual area of interest on the seat 100, the human biofidelic manikin 10 reacts more significantly in response to the application of mechanical stimuli of some frequencies (indicated on the graph by the relatively long vertical lines) than of other frequencies (indicated on the graph by the relatively short vertical lines). For example, the graph indicates that in this single individual area of interest on the seat 100, the human biofidelic manikin 10 reacts more significantly in response to the application of mechanical stimuli having a frequency of about 4.0 Hertz than it does in response to the application of mechanical stimuli having a frequency of about 5.0 Hertz. However, a different individual area of interest on the seat 100, the human biofidelic manikin 10 might react more significantly in response to the application of mechanical stimuli having a frequency of about 5.0 Hertz than it does in response to the application of mechanical stimuli having a frequency of about 4.0 Hertz.

The combined use of the human biofidelic manikin 10 and the pressure distribution sensor array 110 of this invention yields pressure distribution data that has not been heretofore available. As mentioned above, the adoption of new, thinner-foam technologies in seats (such as the illustrated seat bottom 102) has been hampered by a fear that an occupant of the seat would be likely to "bottom out" on an underlying frame when the vehicle is operated over a rough road. The determination of the natural resonant frequency for each of the individual areas of interest on the seat 100 (which, again, are defined by the individual pressure sensors 112*a* and 114*a*) is important because each individual area of interest will react differently in response to not only the magnitude of the mechanical stimuli applied to the associated portion of the human biofidelic manikin 10, but also to the frequency of such mechanical stimuli. Thus, the system of this invention provides a dynamic seating pressure distribution characteristic yielding valuable data to assist in the design of seats that are comfortable under a variety of operating conditions.

Thus, it can be seen that this invention enables a fast, safe, and cost efficient on-road ride simulation that helps predict the complete dynamic requirements for the seat design. The human biofidelic manikin 10 (with its biofidelic mass, mass distribution, shape, skeletal geometry and kinematics, mechanical compliance, and other criteria that match typical humans) provide both a realistic human body pressure distribution trace and a response to vibration that is similar to human subjects. The human biofidelic manikin 10 also enables desirable repeatability associated with engineering manikins.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A system for generating a dynamic seating body pressure distribution data comprising:
   a seat having a plurality of areas of interest, each area of interest having a unique natural resonant frequency;
   a stimulus applying mechanism that is adapted to apply a stimulus of varying frequency to the seat;
   a human biofidelic manikin provided on the seat; and
   a seat pressure distribution sensor array having a plurality of individual pressure sensors, each individual pressure sensor positioned at one of the plurality of areas of interest;
   wherein the seat pressure distribution sensor array is responsive to the human biofidelic manikin for generating a dynamic seating body pressure distribution data when the stimulus applying mechanism applies a stimulus of varying frequency to the seat;
   wherein each area of interest reacts differently in response to the frequency of the stimulus applied to the seat by the stimulus applying mechanism;
   wherein changes in pressure exerted on each area of interest in the seat by the human biofidelic manikin in response to the stimulus of varying frequency applied to the seat over time are measured by the individual pressure sensors, the measurements defining the dynamic seating body pressure distribution data.

2. The system defined in claim 1 wherein the seat pressure distribution sensor array is provided on a surface of the seat, and wherein the human biofidelic manikin provided on the seat pressure distribution sensor array.

3. The system defined in claim 1 wherein the seat pressure distribution sensor array is provided within the seat, and wherein the human biofidelic manikin provided on the seat.

4. The system defined in claim 1 wherein the seat includes a seat bottom and a seat back, the human biofidelic manikin is provided on one of the seat bottom and the seat back, and the seat pressure distribution sensor array is responsive to the human biofidelic manikin on the one of the seat bottom and the seat back.

5. The system defined in claim 1 wherein the seat includes a seat bottom and a seat back, the human biofidelic manikin is provided on both of the seat bottom and the seat back, and the seat pressure distribution sensor array is responsive to the human biofidelic manikin on both of the seat bottom and the seat back.

6. The system defined in claim 1 wherein the individual pressure sensors are arranged in a two-dimensional array.

7. The system defined in claim 1 wherein the dynamic seating body pressure distribution data is expressed as a two dimensional array of individual pressure measurement regions.

8. A method for generating a dynamic seating body pressure distribution data comprising the steps of:
(a) providing a seat having a plurality of areas of interest, each area of interest having a unique natural resonant frequency;
(b) providing a seat pressure distribution sensor array having a plurality of individual pressure sensors, each individual pressure sensor positioned at one of the plurality of areas of interest;
(c) providing a human biofidelic manikin on the seat;
(d) applying a stimulus of varying frequency to the seat; and
(e) generating a dynamic seating body pressure distribution data when the stimulus of varying frequency is applied to the seat;
wherein the seat pressure distribution sensor array is responsive to the human biofidelic manikin for generating a dynamic seating body pressure distribution data when the stimulus of varying frequency is applied to the seat;
wherein each area of interest reacts differently in response to the frequency of the stimulus applied to the seat; and
wherein changes in pressure exerted on each area of interest in the seat by the human biofidelic manikin in response to the stimulus of varying frequency applied to the seat over time are measured by the individual pressure sensors, the measurements defining the dynamic seating body pressure distribution data.

9. The method defined in claim 8 wherein step (a) is performed by providing a seat pressure distribution sensor array on a surface of the seat, and wherein step (c) is performed by providing the human biofidelic manikin on the seat pressure distribution sensor array.

10. The method defined in claim 8 wherein step (a) is performed by providing a seat pressure distribution sensor array within the seat.

11. The method defined in claim 8 wherein step (a) is performed by providing a seat that includes a seat bottom and a seat back, step (c) is performed by providing the human biofidelic manikin on one of the seat bottom and the seat back, and step (e) is performed by generating a dynamic seating body pressure distribution data when the stimulus of varying frequency is applied to the one of the seat bottom and the seat back.

12. The method defined in claim 8 wherein step (a) is performed by providing a seat that includes a seat bottom and a seat back, step (c) is performed by providing the human biofidelic manikin on both of the seat bottom and the seat back, and step (e) is performed by generating a dynamic seating body pressure distribution data when the stimulus of varying frequency is applied to both of the seat bottom and the seat back.

13. The method defined in claim 8 wherein the individual pressure sensors are arranged in a two-dimensional array.

14. The method defined in claim 8 wherein step (e) is performed by expressing the dynamic seating body pressure distribution data as a two dimensional array of individual pressure measurement regions.

* * * * *